United States Patent

Hirschfeld

Patent Number: 5,242,797
Date of Patent: Sep. 7, 1993

[54] NUCLEIC ACID ASSAY METHOD

[75] Inventor: Tomas B. Hirschfeld, Livermore, Calif.

[73] Assignee: Myron J. Block, North Salem, N.H.

[21] Appl. No.: 817,942

[22] Filed: Jan. 2, 1992

Related U.S. Application Data

[60] Continuation of Ser. No. 483,909, Feb. 22, 1990, abandoned, which is a division of Ser. No. 842,146, Mar. 21, 1986, abandoned.

[51] Int. Cl.$^5$ .......................... C12Q 1/68; C12Q 1/70; G01N 33/00; G01N 33/48
[52] U.S. Cl. ............................. 435/6; 435/5; 436/63; 436/94
[58] Field of Search ............................................. 435/6

[56] References Cited

U.S. PATENT DOCUMENTS

| | | | |
|---|---|---|---|
| 3,652,761 | 3/1972 | Weetall | 435/7 |
| 4,133,639 | 1/1979 | Horte | 435/7 |
| 4,447,546 | 5/1984 | Hirschfeld | 435/7 |
| 4,563,417 | 1/1986 | Albarella et al. | 435/6 |
| 4,568,649 | 2/1986 | Bertoglio-Matte | 435/6 |
| 4,582,789 | 4/1986 | Sheldon, III et al. | 435/6 |
| 4,671,938 | 6/1987 | Cook | 435/7 |
| 4,713,362 | 12/1987 | Dattagupta | 435/6 |
| 4,724,202 | 2/1988 | Dattagupta et al. | 435/6 |

FOREIGN PATENT DOCUMENTS 0070687 1/1983 European Pat. Off. .
0131830 1/1985 European Pat. Off. .
2139349 11/1984 United Kingdom .

OTHER PUBLICATIONS

Dilica, K. Understanding DNA and Gene Cloning; John Wiley & Sons N.Y. 1984 p. 121.

Primary Examiner—Scott A. Chambers

[57] ABSTRACT

An assay for polynucleotides employing total internal reflection of excitation radiation at a coating bonded to the surface of an optically conductive glass cell. The coating initially includes single-stranded polynucleotides coupled to individual attachment sites on the surface of the cell, such polynucleotides being complementary, at least in part to the single-stranded form of the polynucleotide that is being assayed. Each molecule of the coupled polynucleotide is connected to the cell surface through a spacer connected to an irreversibly conjugated polyadenine/polythymidine sequence at one end of the coupled polynucleotide.

When the surface of the coated cell is contacted with a sample that contains single-stranded polynucleotide complementary to the bound polynucleotide, renaturation will occur, forming a double-stranded form of the polynucleotide of interest. A fluorochrome dye specific to that double-stranded form is coupled to the latter, the dye including a chromophore that the excitation radiation will excite into fluorescence. The induced fluorescence is then gathered and measured.

17 Claims, 1 Drawing Sheet

NUCLEIC ACID ASSAY METHOD

This application is a continuation of application Ser. No. 07/483,909, filed Feb. 22, 1990, now abandoned, which is a divisional application of my copending application Ser. No. 842,146, filed Mar. 21, 1986 now abandoned.

This invention relates to biochemical assays, and particularly to assays wherein a tag capable of emitting detectable radiation is employed to identify nucleic acid and the measurement of the concentration and cross-correlation of selected nucleic acids and fragments.

A known technique for chemical and biochemical assay, as described in U.S. Pat. Nos. 4,133,639; 4,050,895; 4,321,057; 4,399,099; 4,447,546 and others, incorporates an optical system employing the principles of attenuated total reflection (ATR) spectroscopy. For the ATR cell, such an optical system uses an optical wave guide, typically a plate, rod or optical fiber. When one end of the cell is illuminated with excitation radiation, that radiation is totally internally reflected so as to create an evanescent wave at the cell surface. The excitation radiation is selected so that the evanescent wave will excite fluorescence in substances to be assayed and located in only a thin zone (typically a few hundred to a thousand Angstrom units thick) surrounding the cell surface. The resulting fluorescence can provide information from which the fluorescing material may be assayed. Such systems have hitherto been employed to assay, for example, for antigenic substances, chemicals and the like.

It is also well known that genetic information directing the synthesis of amino acid sequences in protein is carried by deoxyribonucleic acid (DNA) or ribonucleic (RNA), both very long, complex molecules usually in the form of a double-helix. Because DNA or RNA are ubiquitous in all living matter in forms unique to each species, the nature of the nucleic acid or unique fragments thereof (all collectively hereinafter referred to as polynucleotides) can serve to assay for the presence of a given species. For example, all viral genes contain either RNA or DNA. Such viral nucleic acids can be easily isolated from the protein coat or shell and are presently available in highly purified form. Many of the viral nucleic acids are linear and double-stranded (DNA in such viruses as smallpox and SV40 for example, and RNA in such viruses as the reoviruses). Single-stranded nucleic acids can always become double-stranded if complementary single-strands are available. The double strands of nucleic acid can be separated by subjecting the nucleic acid to denaturing conditions (e.g., high or low pH, high temperatures, reagents such as EDTA and quanidine that breaks hydrogen bonds, etc.). Denaturing not only usually separates the nucleic acid into single strands but also can be made to break the strands into a large, unpredictable assortment of fragments that are extremely difficult to separate from one another in identifiable form. Often, restriction enzymes are used to break nucleic acids at specified sites to create a multiplicity of fragments that are laboriously separated by electrophoretic and other time-consuming techniques for eventual identification.

A principal object of the present invention is to provide apparatus for and a method of assaying for polynucleotides or nucleic acid moieties, which apparatus and methods permit one to unambiguously and quickly identify the genetic source of the moiety. Another important object of the present invention is to provide such apparatus and method that may be used directly upon a sample of containing nucleic acid fragments without first separating the fragments into homogeneous groups. Yet another object of the present invention is to apply to the problem of detection and identification of nucleic acids, the sensitivity and simplicity of fluorescence assays employing optical fibers.

These and other objects are met in the present invention of apparatus and methods for fluorescent assay of polynucleotides or nucleic acid fragments or moieties secured to or bonded to the surface of an elongated attenuated total reflection (ATR) cell. Any double-stranded nucleic acid in the sample to be assayed is denatured, e.g., by heating to ca. 80° C., to form single strands of the nucleic acid. Denaturation can be aided by adding chelators to remove stabilizing ions such as $Mg^{++}$. The single strands may broken into sequences of desired length by known appropriate restriction enzymes. Selected moieties of single-strands of double-stranded nucleic acid characteristic of the species to be identified, separated for example by liquid chromatography or electrophoresis, are secured on the less optically dense side of an interface to be formed between media of differing refractive index (e.g., an ATR cell in the form of a prism, rod or fiber optic element, and a fluid sample suspected of containing the nucleic acid to be assayed). The sample is now gradually cooled in contact with the interface; to the extent that a portion of the single-strands of nucleic acid in the sample are complementary to the single-stranded nucleic acid moiety initially bound to the interface, a portion of the bound nucleic acid will be hybridized with the sample nucleic acid.

Whatever polynucleotides have renatured with the bound moieties on the surface of the cell, may now be stained with a fluorochrome dye specific for double stranded polynucleotides (e.g., preferably in dimeric form to increase specificity and binding stability). Alternatively, for competition binding, one may use pre-tagged complementary single strands of the polynucleotide, the presence of which is being assayed in the sample. Partial matches can be discriminated against by adding at this point an enzyme that cleaves the double helix wherever single-strand fragments in the sample do not form a double-strand with the bound moieties. One end of the cell is then illuminated with excitation radiation that is totally internally reflected within the cell so as to create an evanescent wave at the ATR cell surface. The excitation radiation is selected so that the evanescent wave will excite the fluorochrome on the dyed polynucleotides in only the thin zone surrounding the ATR cell surface. If the chain length fits within the zone illuminated by the evanescent wave, the resulting fluorescence is a measure of the double stranded polynucleotides bound to the cell surface, and hence, a measure of the nucleic acid in the sample complementary to the nucleic acid pre-loaded onto the ATR cell. Fluorescent lifetime measurements can also permit the quantum efficiency of the fluorochrome, and hence the degree of matching between the polynucleotides initially bound to the interface and those complexed to it from the sample, to be measured. This allows one to distinguish among emissions from specifically bound dye, atypically or less specifically bound dye and unbound dye, thus improving signal-to-background ratios.

Other objects of the invention will in part be obvious and will in part appear hereinafter. The invention accordingly comprises the apparatus possessing the construction, combination of elements, and arrangement of parts and the process involving the several steps and the relation and order of one or more of such steps with respect to each of the others which are exemplified in the following detailed disclosure and the scope of the application all of which will be indicated in the claims.

BRIEF DESCRIPTION OF THE FIGURES

For a fuller understanding of the nature and objects of the present invention, reference should be had to the following detailed description taken in connection with the accompanying drawings in which like index numbers refer to like elements, wherein FIG. 1 is a longitudinal cross-section of an assay kit incorporating the principles of the present invention.

Figure 1:
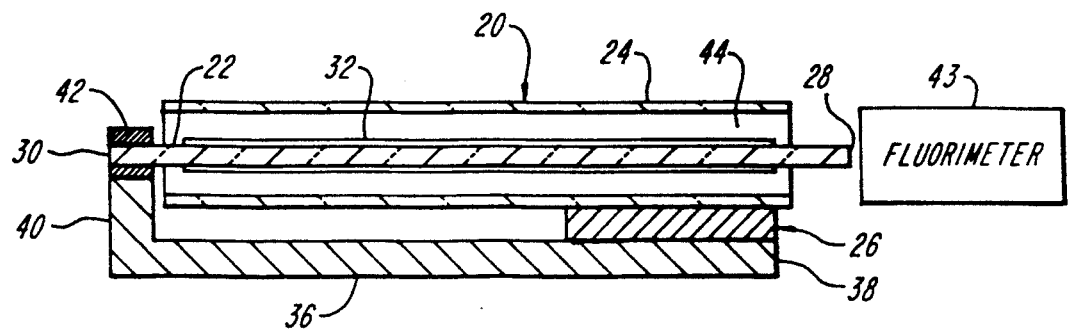
FIG. 1 is a longitudinal cross-section of an assay kit for the practice of the claimed method.
Figure 2:
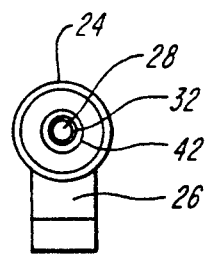
FIG. 2 is an end view of the embodiment of FIG. 1.

It should be noted that in the detailed description of the apparatus of this invention, reference to portions of the apparatus as "upper" and "lower" is wholly for convenience and to relate the description to the diagrammatic representations in the drawings. It will be appreciated that the apparatus can function in any position or orientation and it is within the scope of this invention to do so. It is further to be understood that the representation in the FIGS. is diagrammatic and that no attempt has been made to indicate actual scales or ratios.

The present invention operates by totally internally reflected excitation radiation along an ATR cell, which excitation excites fluorescence that tunnels back into the cell, and the detection of that fluorescence, all as generally described in U.S. Pat. No. 4,582,809 issue Apr. 15, 1986, and assigned to the assignee of the present application, and to which reference may be had for further details of the optical mode of operation of the invention.

In FIG. 1 there is shown in longitudinal cross-sectional view assay kit 20 made in accordance with the principles of the present invention. In a preferred embodiment, kit 20 comprises ATR cell 22, enclosure 24, and mounting means 26.

Cell 22 is preferably an elongated, substantially cylindrical, optically-transparent body typically in the form of a rod or optical fiber extending from its proximal end or entrance face 28 to a distal or terminal end 30. Cell 22 is adapted to propagate along its length, through multiple total internal reflections, optical radiations entering face 28 within an established solid angle substantially rotationally symmetric about the cell's longitudinal axis. Where the cell is a fiber as shown in FIG. 1 (and for purposes of exposition, cell 22 will be hereinafter referred to in this context), as is well known in the art of fiber optics, the maximum acceptance angle with regard to the fiber axis, B, for the radiation entering the fiber and so propagating within it, is established by the refractive indices of the fiber and the surrounding medium. At face 28 the fiber surface typically is planar, is disposed normally to the long axis of the fiber and is preferably highly polished to minimize blemishes or surface defects that would tend to scatter incident excitation radiation.

For radiation initially propagating through a medium of refractive index $n_0$, incident upon a fiber of refractive index $n_1$, otherwise surrounded by a material of refractive index $n_2$, the maximum acceptance angle is as shown in the following equation:

$$NA = n_0 \sin B = (n_1^2 - n_2^2)^{\frac{1}{2}} \quad (1)$$

wherein NA is the so-called numerical aperture of the fiber. By way of example, but not limitation, fiber 22 may be any of a large number of optically transparent materials, such as glass, quartz, polypropylene, polyolefin, nylon, or the like, chosen to have an index of refraction greater than that of the fluid sample being assayed. The latter is typically, an aqueous solution having an index of refraction near 1.33. It will further be appreciated that the material of fiber 22 is also chosen to be relatively insoluble in and non-reactive with the sample fluid. While the size of fiber 22 may be varied as desired, it has been found that a fiber or rod from about 1 mm to a few hundred microns diameter by as little as 5 mm in length is adequate for most assays, it being understood however, that such length and diameter are merely exemplary and not limiting.

In a preferred embodiment in which the fluorescence, induced at the the fiber surface by excitation radiation launched down the fiber, is collected or observed at the same proximal end of the fiber at which the excitation radiation is injected, it is desired to prevent stray radiation from going back down the fiber from face 30 to face 28. Consequently, face 30 may be shaped to spill out light incident thereon internally, but preferably is coated with a material matching the index of refraction of the medium surrounding face 30, such material being both non-fluorescent and aborbent with respect to the excitation radiation. Typically, an epoxy resin loaded with carbon black serves such function.

In an exemplary embodiment, it is intended that the operative portion of the fiber surface be defined by the activated region at which the assay is to be performed. To activate the surface of the operative portion of fiber 22, the latter is typically treated to provide coating 32 by first binding an aromatic amine to the fiber surface as an agent to provide a diazo coupling to the single stranded nucleic acid or polynucleotide. The aromatic amine should be coupled to the surface of the fiber through a spacer so that the amine is free to react without being sterically hindered by the glass. A number of such spacer coupling techniques that can be employed are well known as shown in the following Examples:

EXAMPLE I

The hydroxyl moities on the glass surface (hereinafter identified as "G") can be coupled with trimethoxysilane substituted with a chain of methylene groups having an aromatic amine group at the end, typically

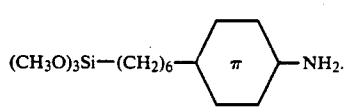

This reagent is commercially available from Petrarch Chemical Company. The reagent, when in solution preferably buffered to pH8; will react with the hydroxyl groups on the glass (G) to eliminate methanol and form a siloxane bond as follows:

(1) $G(OH)_3$ and

-continued

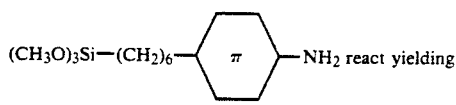 react yielding

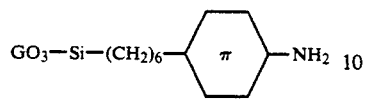

EXAMPLE II

Alternatively, one may couple the glass surface with a reagent formed of two epoxy groups connected by a methylene chain. For example, using an excess of the reagent in a highly alkaline solution (typically NaOH) to prevent too many of both ends of each reagent molecule from coupling with the glass, the following reaction will occur to form an ether linkage:

(2) GOH and

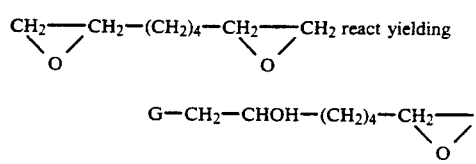

If now the latter intermediate is reacted with a sulfhydryl or thiol, one forms a thioether linkage as follows:

(3) 

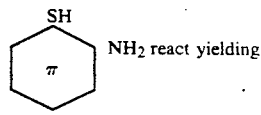 react yielding

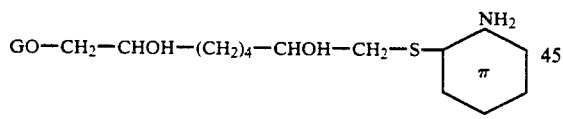

EXAMPLE III

Yet another coupling may be achieved through an aliphatic amine linkage as follows:

(4) $G(OH)_3$ and $(CH_3O)_3-Si-(CH_2)_3-NH_2$ react yielding $GOSi-(CH_2)_3-NH_2$ To the foregoing reaction product one adds at pH8, excess double isothiocyanate with an intermediate methylene chain to form a thiourea linkage:

(5) $GO_3Si-(CH_2)_3-NH_2$ and $NCS-(CH_2)_6-NCS$ react yielding

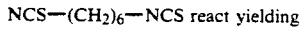
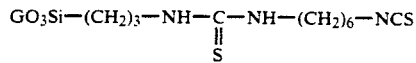

Adding an excess of double aromatic amine at pH8 completes formation of the desired aromatic, i.e.

(6) 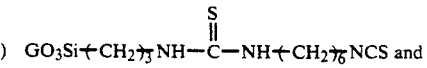 and

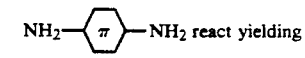 react yielding

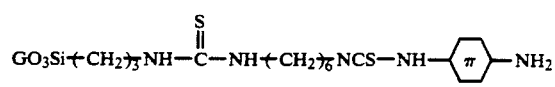

EXAMPLE IV

A fourth glass coupling technique yielding an unusually stable product is to treat the glass at pH8 with a trimethoxysilane having a chlorobenzyl group:

(7) GOH and

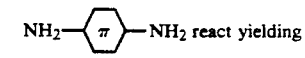 react yielding

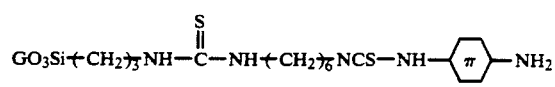

The reaction product is reacted at pH9 with an aromatic amine having a nitro group:

(8)  and

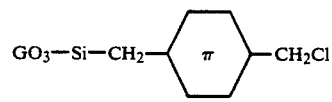 react yielding

Thence, the reaction product is treated with a strong reducing agent such as sodium dithionite at pH6 to reduce the nitro group to an aromatic amine as follows:

(9) 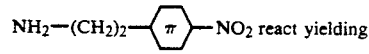 and $Na_2S_2C_4$ react yielding

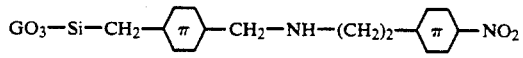

The aromatic amine produced by any of the foregoing techniques can be used to bind the desired single-stranded nucleic acid. As a preliminary step, one should treat the aromatic amine bound to the glass (hereinafter

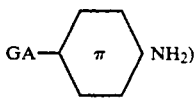

with nitrous acid (acid nitrite solution) around 0° C. This produces an intermediate which is then reacted at pH8 with poly-T (hereinafter (TTT), a known synthetic DNA, the only base of which is thymidine), all as described as follows:

(10) 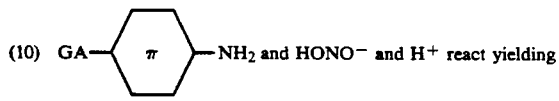

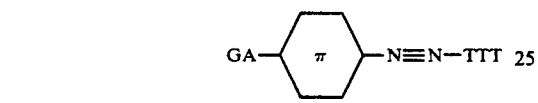

It is known that cells tend to produce strands of nucleic acid spaced apart with short strands of polyadenine. Hence the latter product is now reacted with the adenine moiety typically present at the beginning of a single-stranded nucleic acid molecule (hereinafter AAA-NUC) of interest that is to form the nucleic acid moiety bound to the fiber surface. Inasmuch as adenine is the conjugate of thymidine, the latter will double-strand in the presence of Mg+ at pH7 at room temperature, to form a bond.

(11) 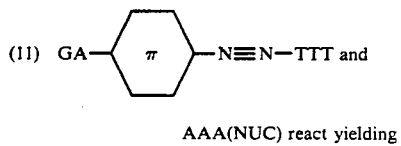

AAA(NUC) react yielding

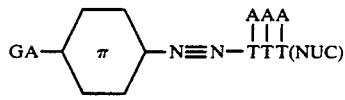

The double stranded bond can now be made permanent by treating the adenine-thymidine conjugates with psoralen (6-hydroxy-5-benzofuranacrylic acid δ-lactone) or other cross-linking agent. Psoralen is preferred for it is relatively non-volatile and is readily activated by ultraviolet radiation. For proper hybridization, the bound DNA segment should be at least 10 bases long, although a greater number may be required for reasonable specificity. It will be seen that this technique binds that portion of the DNA not used in its recognition, i.e. the polyadenine chain at the beginning. The purpose of so doing is to avoid problems arising out of possible binding of the diazo linkage to part of the recognition sequence of the bound single-stranded nucleic acid. In other words, the reaction with psoralen allows attachment to one end of the nucleic acid sequence without plugging the recognition site. But for the reinforcement provided by psoralen treatment, denaturation would break the acid. Of course, if the foregoing type of problem is not expected to arise, one may eliminate this extra step.

The concentrations of chemicals employed to form coating 32 depends empirically upon the particular type of coating linkage to be formed and the nature of the nucleic acid moiety one desires to bind in the coating. However, it should be noted that the reactive sites (i.e. those sites on the fiber at which the coating contains the bound single stranded nucleic acid moieties with which one intends to hybridize complementary nucleic acid fragments) should, on the average, be spaced apart several (e.g. three or more) times the average 10A diameter of a typical DNA double strand. If the concentration of sites is less dense, the ultimate hybridization reaction with the coating will be spatially or sterically hindered and thus may proceed too slowly for many purposes.

The foregoing binding procedure has a number of desirable characteristics. It provides a strong bond to glass. This bond is irreversible even under denaturation conditions and is photostable. The provision of a spacer between the ATR surface and the molecular chain allows easy access (for reasonable diffusion kinetics) and enough room for the chain flexures that are part of the hybridization process. The poly A-poly T link insures that the chain will be bound at a single location thereby preserving the chain flexibility need for reasonable hybridization kinetics. This link also insures that the recognition site is excluded from the binding location.

Enclosure 24 is a hollow, elongated tube, preferably but not necessarily optically transparent, and formed of a material that is relatively insoluble and chemically non-reactive with the fluid being assayed. Typically enclosure 24 is simply a glass tube having an inside diameter greater than the maximum outside diameter of fiber 22, and preferably dimensioned to delimit a predetermined volume surrounding at least activated coating 32 on fiber 22. In a preferred embodiment, the interspace between the coated surface of fiber 22 and the inside wall of enclosure 24 may be of capillary dimensions.

Mounting means 26 are provided for holding fiber 22 and enclosure 24 in a fixed relation in which, particularly, the enclosure is spaced from the fiber so that the predetermined delimited volume of sample may surround the activated region on the fiber surface, and the input end of the fiber is held precisely to permit optimum light injection into the fiber. Consequently, the fiber may be held by the mounting means adjacent either face 28 or face 30. However, contact between the fiber and the mounting means adjacent face 28 tends to reduce the numerical aperture inasmuch as the refractive index of the mounting material is generally higher than $n_1$. To alleviate this problem, typically the fiber may be coated, at least near the end of the fiber into which radiation is propagated, with a cladding, typically of a transparent, high-molecular weight polymer disposed to provide an interposed, low-refractive index medium between the mounting and the fiber. To avoid problems due to mounting adjacent the proximal end of the fiber, the mounting means in FIG. 1 is shown simply as cradle 36 having one portion 38 thereof coupled to and supporting enclosure 24, another portion 40 thereof being coupled to and supporting ferrule 42 in which distal end 30 of fiber 22 is firmly mounted. The material out of which ferrule 42 is formed is not important from a standpoint of optics, but should be relatively non-reactive chemically with the fluid sample to be assayed. In the embodiment of FIG. 1, enclosure 24 and fiber 22 are shown mounted so that the long axes of both the enclosure and fiber are substantially horizontally, with fiber 20 being thus cantilevered to extend internally within enclosure 24 with end 28 protruding outwardly therefrom, fiber 22 being maintained in spaced relation to the internal surface of enclosure 24. In this particular embodiment, enclosure 24 is open at both ends, thereby permitting fluid to be introduced or withdrawn from either end.

In operation of the embodiment of FIG. 1, coating 32 of fiber 22 is formed from any of a number of single stranded nucleic acid moieties. The latter are bound as hereinbefore described to provide attachment sites for the sample nucleic acid moieties to the fiber, and the attached moieties are then measured by staining.

The sample is first treated by known techniques to concentrate the potential nucleic acid (if necessary) and then the viral capsids or biological cellular structures are lysed, as by osmotic shock, detergent or other lysing agents to release nucleic acids. The sample is then subjected to treatment that will denature any double-stranded nucleic acid released and will break the nucleic acid chain into fragments. For example, double stranded DNA can be denatured simply by treatment with gentle heat (75° C.) and EDTA. The use of EDTA also removes $Mg^{++}$ ions if the latter are present either from the sample or the polyadenine/thymidine binding step; such removal is highly desirable to prevent the metal ions from renaturing the single stranded nucleic acid. Of course, one may employ known enzymatic DNA splitting techniques to fragment the nucleic acid. The order in which fragmentation and denaturation occur is not important to the present invention.

The sample is then injected into interspace 44 between enclosure 24 and fiber 22 is filled, as with a hypodermic syringe, the sample being held in interspace 44 by the meniscuses formed at opposite ends of enclosure 24. The sample is allowed to incubate in interspace 44 as desired to permit the material being assayed in the fluid sample to diffuse to and renature or complement the nucleic acid moieties in coat 32. The reversibility of nucleic acid conjugation reactions provides an avidity controlled limit to system sensitivity, particularly if the system is washed out to remove merely absorbed but unconjugated nucleic acid. This difference in avidity between absorption and conjugation can be increased if prior to washing, compounds of the psoralen family are added to the sample. Such compounds will bind to double-stranded nucleic acid regions and upon exposure to light will serve to cross-link irreversibly those double-stranded regions.

The double-stranded renatured nucleic acid is dyed preferably by spiking the sample solution directly with a fluorochrome dye having a large avidity and specific to the double-stranded nucleic acid. The preferred dyes have more than one independent nucleic acid binding site to increase avidity and thus reduce the free dye concentration and background. Typical dyes useful in the present invention are ethidium bromide, acridine orange (C.I. No. 46005), quinacrine, diethidium bromide, diacridine orange, the various heterodimers, and the like. Ethidium bromide has an optimum excitation wavelength range of 480 to 550 $\mu$m and optimum fluoresence wavelength range of 580 to 650 $\mu$m. The structure of ethidium bromide is believed to be as follows:

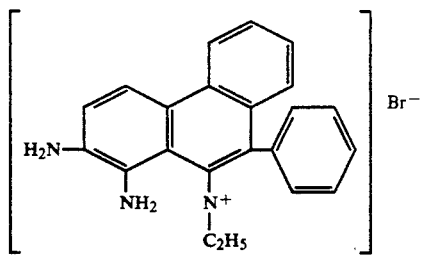

Alternatively, to reduce possible reagent instability, the dye can be provided initially in a form very weakly prebound only to the fiber so that it will release in water in milliseconds. The dye chosen is preferably one, the fluorescent signal from which is strongly affected by the binding and thus by the degree to which both nucleic acid chains are hybridized; such dyes are commonly known as fluorochrome dyes. For fluorochrome dyes such as ethidium bromide and acridine orange or their dimers, the concentration required for the sample in interface 44 can be low, i.e. between about $10^{-10}$ and $10^{-14}$M.

It should be noted that the surface of the solution injected into interspace 44 is believed to contain about six orders of magnitude more of single stranded nucleic acid than is present in the bulk of the solution. Hence, there will be a higher nucleic acid recombination rate at the interface of the solution and the fiber, and the dye will preferentially bind to the double strands formed on the fiber, which strands are the only ones illuminated. The dye is free-floating prior to the reaction between the nucleic acid under test and the reagent on the fiber, and is a tag for only the conjugated form. Because the dye is a fluorochrome, it is inherently less efficient unbound than bound. The use of the dimeric form of the dye serves to provide stronger binding which squares the avidity of the dye for the double stranded nucleic acid. Hence with dimeric dyes, one obtains an increase in selectivity to double-stranded DNA, and a lowered background because less free dye is required in the bulk of the solution, thereby providing a very high signal-to-noise ratio.

The apparatus is coupled to fluorimeter 43 so that entrance face 28 is illuminable with radiation, typically capable of exciting or inducing fluorescence in coat 32 by an evanescent wave accompanying the transmission of the radiation down the fiber. The fluoresence induced in the tagged complex at coat 32 then tunnels back into the fiber from the excited material and then out through face 28 to be read by fluorimeter 43. The intensity of the fluorescence will be proportional to the amount of double-stranded nucleic acid present and thus is a function of the relative amount of matching nucleic acid present in the original sample.

There will be an error in the foregoing data caused by the variation in quantum efficiency of the dye, which may reflect the degree of perfection of the hybridization match. One way to correct such an error is to make a supplementary measurement of the fluorescence lifetime which is proportional to the quantum efficiency. The ratio of signal intensity to lifetime is independent of the quantum efficiency and thus free of the error. The actual lifetime values also can serve as a measure of the degree of correlation of the nucleic acid strands with one another.

The natural fluorescence lifetime can be defined as the time required for the fluorescence to decay, following cessation of excitation, from its maximum I to a value of I/e where e is the Naperian base. Using known techniques and apparatus, the fluorescence lifetime can be determined by first illuminating the material with rapidly modulated excitation radiation for the fluorochrome dye employed, for example, radiation of fluctuating amplitude as from a laser or a sub-threshold LED, and then measuring the modulation amplitude of the fluorescence generated.

An alternative method of assaying with the apparatus of the present invention, is to perform a competition-binding type of assay. In the latter, a known amount of the single stranded polynucleotide sought to be identified or measured, is tagged in known manner, preferably with any of a large number of known functionalized fluorescent dyes. A first measurement is made of the total fluorescent radiation from such tagged quantity by a suitable fluorimeter for calibration purposes. A known amount of the tagged polynucleotide is then added to the sample solution. The mixture of tagged and untagged polynucleotides is then placed in contact with an ATR cell allowed to compete for hybridization sites, the cell being prepared and illuminated as above described. A measurement is then made of the fluorescence intensity from the cell. The ratio of the latter fluorescence intensity to the intensity measured during calibration is then proportional to the amount of untagged polynucleotide present in the sample.

Since these and certain other changes may be made in the above method and apparatus without departing from the scope of the invention herein involved, it is intended that all matter contained in the above description or shown in the accompanying drawings shall be interpreted in an illustrative and not in a limiting sense.

What is claimed is:

1. A method of assaying a liquid sample for a polynucleotide of interest in single-stranded form, said method consisting of the steps of:
   bonding a first single-stranded polynucleotide to a surface of an optically-transmissive, attenuated total internal reflection cell, said first single-stranded polynucleotide being complementary, at least in part, to said polynucleotide of interest;
   adding to said cell a fluorochrome dye that yields a fluorescence signal which is strongly affected by the degree of hybridization of the polynucleotide, said dye binding preferentially to a double stranded polynucleotide as compared with a single stranded polynucleotide, said binding causing a greater efficiency of fluorescence as compared with the unbound state;
   contacting said surface having said first polynucleotide bound thereto with said sample containing a single stranded polynucleotide of interest under conditions sufficient for any single-stranded polynucleotide which is complementary to said bound first polynucleotide to hybridize with said bound first polynucleotide;
   coupling said fluorochrome dye to said hybridized polynucleotide on said cell surface;
   internally illuminating said cell with excitation radiation so as to generate, adjacent to said surface, an evanescent wave which interacts with said fluorochrome dye to induce fluorescence from said fluorochrome dye;
   collecting fluorescent radiation arising from excitation of said fluorochrome dye and exiting from an end of said cell; and
   measuring the collected fluorescent radiation wherein said fluorescence is indicative of hybridization of the single stranded complementary polynucleotide and the single stranded polynucleotide of interest, thereby indicating the presence of the single stranded polynucleotide of interest.

2. The method as defined in claim 1 wherein said step of contacting said surface comprises the further step of adding a known quantity of said single stranded polynucleotide of interest with a fluorescent dye coupled thereto to said sample prior to contacting said surface with said sample, so that said single-stranded polynucleotide with said fluorescent dye will compete with single stranded polynucleotide of interest originally in said sample in said hybridization.

3. The method as defined in claim 1 wherein said bonding step includes binding an aromatic amine to said surface, and then diazo coupling said aromatic amine to said selected single-stranded polynucleotide.

4. The method as defined in claim 3 wherein said aromatic amine is coupled to said surface through a spacer molecule.

5. The method as defined in claim 4 wherein said spacer is a trimethoxysilane substituted with a chain of methylene groups.

6. The method as defined in claim 4 wherein said spacer is formed of a pair of epoxy groups connected by a methylene chain.

7. The method as defined in claim 4 wherein said spacer is an aliphatic amine.

8. The method as defined in claim 4 wherein said spacer is a trimethoxysilane having a chlorbenzyl group.

9. The method as defined in claim 3 wherein said diazo coupling is formed by first converting said amine to a diazo group, coupling said diazo group to a polythymidine, and conjugating said polythymidine with a polyadenine moiety present at the beginning of said selected single-stranded polynucleotide.

10. The method as defined in claim 9 wherein said amine is converted to a diazo group by treatment with a diazonium halide.

11. The method as defined in claim 9 including the step of cross-linking said polyadenine with said polythymidine.

12. The method as defined in claim 9 wherein the step of measuring comprises measurement of the intensity of said fluorescent radiation.

13. The method as defined in claim 9 wherein the step of measuring comprises measurement of the fluorescent decay lifetime of said fluorescent radiation.

14. The method as defined in claim 1 wherein said fluorochrome dye is selected form the group consisting of ethidium bromide, acridine orange, diethidium bromide, diacridine orange, and quinacrine.

15. The method as defined in claim 14 wherein said dye is ethidium bromide or its dimers.

16. The method as defined in claim 14 wherein said dye is acridine orange or its dimers.

17. A method of assaying a liquid sample for a polynucleotide of interest in single-stranded form, said method consisting of the steps of:

placing said sample in an optically-transmissive, attenuated totally internally reflecting cell having immobilized on a surface thereof a coating including a first single-stranded polynucleotide complementary, at least in part, to said polynucleotide of interest;

adding a fluorochrome dye that binds preferentially to the double-stranded form of said polynucleotide of interest as compared to said single-stranded form, said binding causing a greater efficiency of fluorescence as compared with the unbound state forming a complex of said double-stranded polynucleotide and said fluorochrome dye;

propagating an evanescent wave within said cell radiation which excites fluorescent radiation upon interaction with said fluorochrome dye, and detecting said fluorescence from said fluorochrome dye wherein said fluorescence is indicative of hybridization of the single stranded complementary polynucleotide and the single stranded polynucleotide of interest, thereby indicating the presence of the single stranded polynucleotide of interest.

* * * * *